US012240809B2

(12) United States Patent
De Haan et al.

(10) Patent No.: US 12,240,809 B2
(45) Date of Patent: Mar. 4, 2025

(54) COMPOSITION OF BHET AND USE THEREOF

(71) Applicant: Ioniqa Technologies B.V., Eindhoven (NL)

(72) Inventors: Andre Banier De Haan, Eindhoven (NL); Joost Robert Wolters, Eindhoven (NL); Michael Josef De Groot, Eindhoven (NL); Jannigje Maria Jacomina Gravendeel, Eindhoven (NL)

(73) Assignee: Ioniqa Technologies B.V. (NL)

( * ) Notice: Subject to any disclaimer, the term of this patent is extended or adjusted under 35 U.S.C. 154(b) by 576 days.

(21) Appl. No.: 17/634,139

(22) PCT Filed: Aug. 20, 2020

(86) PCT No.: PCT/EP2020/073308
§ 371 (c)(1),
(2) Date: Feb. 9, 2022

(87) PCT Pub. No.: WO2021/032826
PCT Pub. Date: Feb. 25, 2021

(65) Prior Publication Data
US 2022/0267248 A1    Aug. 25, 2022

(30) Foreign Application Priority Data

Aug. 22, 2019    (NL) ..................................... 2023686

(51) Int. Cl.
*C07C 67/52*    (2006.01)
(52) U.S. Cl.
CPC .......... *C07C 67/52* (2013.01); *C07B 2200/13* (2013.01)

(58) Field of Classification Search
CPC ............................... C07C 67/52; C07C 69/82
See application file for complete search history.

(56) References Cited

U.S. PATENT DOCUMENTS

| | | | | | |
|---|---|---|---|---|---|
| 3,607,908 | A | * | 9/1971 | Enoki ..................... | C07C 67/60 560/79 |
| 3,666,791 | A | * | 5/1972 | Chikawa ................ | C07C 69/82 560/79 |
| 3,668,235 | A | * | 6/1972 | Ichikawa ............... | C07C 67/52 560/93 |
| 7,030,264 | B1 | * | 4/2006 | Inada ...................... | C08J 11/24 560/96 |
| 2018/0319950 | A1 | * | 11/2018 | Parrott .................... | C08J 11/26 |

FOREIGN PATENT DOCUMENTS

EP    723951 A1 *  7/1996  ............ C07C 67/03

OTHER PUBLICATIONS

International Search Report re application No. PCT/EP2020/073308, dated Sep. 9, 2020.
Written Opinion re application No. PCT/EP2020/073308, dated Sep. 9, 2020.

* cited by examiner

*Primary Examiner* — Yate' K Cutliff
(74) *Attorney, Agent, or Firm* — Husch Blackwell LLP

(57) ABSTRACT

The invention relates to a solid composition comprising at least 90.0 wt. % bis(2-hydroxyethyl) terephthalate (BHET), as based on dry weight and having a pore volume in the range of 0.20 to 1.0 cm3/g. The porosity is above 25% or even above 35%. The solid composition is made by crystallisation, followed by granulation and fluid bed drying.

19 Claims, 1 Drawing Sheet

COMPOSITION OF BHET AND USE THEREOF

This application is a 371 of international application PCT/EP2020/073308 filed on Aug. 20, 2020 which is incorporated herein by reference.

FIELD OF THE INVENTION

The invention relates to a composition of bis-(β-hydroxyethyl) terephthalate and a process of preparing a solid composition of bis-(β-hydroxyethyl) terephthalate.

BACKGROUND OF THE INVENTION

Bis-(β-hydroxyethyl) terephthalate, hereinafter also referred to as BHET and bis-(2-hydroxyethyl) terephthalate, is a monomer compound for the manufacture of polyethylene terephthalate (i.e. PET). BHET can be produced by ester-interchange between dimethyl terephthalate and ethylene glycol, by direct esterification of terephthalic acid with ethylene glycol and by means of an ethylene oxide process wherein terephthalic acid is directly reacted with ethylene oxide. Again a further process involves the reaction of terephthalonitrile and water with ethylene glycol. However, in view of the huge amount of PET, there is an enormous interest in the recycling of PET into BHET. This can be achieved by catalytic glycolysis.

It is known that the drying of BHET is problematic. As explained in U.S. Pat. No. 3,668,235 of Jun. 6, 1972, when wet BHET is dried under reduced pressure at relatively low temperatures such as 40-60° C., the drying requires objectionably long time, and quality of BHET is degraded by such phenomenon as colouring. However, in attempts to dry the solid BHET by heating to relatively high temperatures of 60-90° C., the surfaces of BHET become sticky and the BHET tends to agglomerate into blocks before completion of its drying. The said patent therefore proposes to melt the solid BHET and evaporate the volatile medium (which wets the BHET) from the melt. Thereto, the wet BHET is to be heated to a temperature of 90-180° C. This step evidently adds significant costs to the production of BHET.

It is therefore not a real surprise that the BHET is currently replaced by purified terephthalic acid as a monomer in the manufacture of PET. However, BHET is obtained as the monomer in the depolymerisation of PET by means of glycolysis. In this situation, it needs to be produced in a dried form that has an appropriate product quality and that can be transported. As mentioned in U.S. Pat. No. 7,030,264, BHET from depolymerisation of PET often contains many impurities that would hamper the use thereof in fresh polymerisation, and is also called 'crude BHET'. The said patent mentions that when such crude BHET is subjected to evaporation or distillation, a condensation reaction will occur, which makes it difficult to obtain high-quality BHET. Therefore, the evaporation or distillation at a temperature of 130-250° C. and a reduced pressure is to be preceded by decationization and/or dianionization. Furthermore, a plurality of BHET crystallisation and recrystallisation steps is needed, with ethylene glycol as a main solvent.

U.S. Pat. No. 7,030,264 however addresses rather the process to obtain a pure BHET with a purity of at least 98.0 wt. %. It remains silent on any drying process. Furthermore, even if the BHET obtained after the distillation and/or evaporation process would be dry—which is not clear—the overall process is cumbersome and costly, in view of the desired recrystallisation and the prescribed distillation and/ or evaporation. In fact, as shown on the website of the applicant (http://www.prt.jp/en.html), the distilled BHET is subsequently polymerised into PET. PET granules constitute the final product, rather than dried BHET. This immediate re-polymerisation however has the disadvantage that it is more difficult to tune the polymerisation process to generate a PET material that can be expanded in stretch-blow moulding process in optimum manner. PET is nowadays used for a variety of food applications, including carbonated drinks with bottles from 0.5 to 2 litres, beer tanks with a volume of 5 or more litres and other packages. It would be preferable to provide BHET in a solid form that can be transported from a depolymerisation plant to a PET polymerisation plant and can therein be used as a starting material, possibly in combination with further ingredients.

SUMMARY OF THE INVENTION

It is therefore an object of the invention to provide an alternative solid form of high-quality BHET and a process for its preparation.

According to a first aspect, the invention provides a solid composition comprising at least 90.0 wt. %, bis(2-hydroxyethyl) terephthalate (BHET), as based on dry weight of the composition, and having a pore volume in the range of 0.20 to 1.0 $cm^3/g$.

According to a second aspect, the invention provides a method of preparing a solid composition comprising at least 90.0 wt. % bis(2-hydroxyethyl) terephthalate (BHET), as based on dry weight of the composition, and having a pore volume in the range of 0.20 to 1.0 $cm^3/g$ comprising the steps of: (1) providing crystalline material comprising at least 90.0 wt. % BHET, based on dry weight of the solid composition; (2) granulating the crystalline material and (3) fluid bed drying of the granulated crystalline material.

According to a third aspect, the invention relates to the use of the solid composition of the invention in the polymerisation of BHET to polyethylene terephthalate.

The inventors have obtained a solid BHET composition of high purity that is suitable for polymerisation into PET and that can be transported. The BHET composition of the invention is characterized by means of its high pore volume and sufficient purity, of at least 90.0 wt. %, preferably of at least 95.0 wt. % and more preferably at least 97.0 wt. %. Its stickiness turns out low and the product is white. Moreover, its use for polymerisation is enabled in that its rate of dissolution in either ethylene glycol or in molten BHET is high, more particularly better than with other sources of BHET. The high pore volume is preferably obtained by means of granulating followed by fluid bed drying. The term 'solid composition comprising BHET' is used in the context of the present invention to refer to a composition in solid form that primarily or even substantially consists of BHET. It is however not excluded that the solid composition comprises contaminants in addition to BHET. Typical contaminants include other terephthalate monomers, such as the BHET-isomer known as iso-BHET (ethylene isophthalate) and hydroxyethyl terephthalate, as well as dimer of BHET.

A comparatively large pore volume was obtained in experiments leading to the invention, when compared to commercially available BHET and a comparative example obtained with a different drying technique. The large pore volume is very advantageous in order to reduce melting time of the BHET into a molten BHET and dissolution times into solvents. A most preferred solvent for the polymerisation into polyethylene terephthalate is ethylene glycol, but other solvents and/or other polymerisation reactions are not excluded. Notwithstanding the comparatively large pore volume, the solid composition had a sufficient strength so that the solid composition did not fall apart into powder. The latter is undesired, as it hampers transportation.

Preferably, the solid composition is in a granule form, having a main size in the range of 0.1 to 10 mm, such as 0.5 to 8 mm, or even a fraction thereof in the range of 3 to 7 mm as defined by sieving. The provision of the solid composition in such a granule form has been found to provide excellent manner for drying and for flowability.

It is an advantage of the present method that the purity of the resulting composition of BHET may be enhanced. Fluid bed drying makes use of a carrier gas. Droplets of liquid may be transported out of the solid composition with the carrier gas. The liquid within the solid composition is or comprises mother liquid which contains contaminations. Hence by transporting the liquid out of the composition rather than merely evaporating the liquid, the overall purity may be enhanced. In an advantageous embodiment, the solid composition is dried in fluid bed drying to a humidity content of at most 5 wt. % (as based on the total weight of the solid composition). Such a humidity level significantly reduces the risk of forming agglomerates, which tend to disturb free flow of the material. More preferably, the humidity content is at most 2 wt. % or even at most 1 wt. %. Much lower humidity contents of less than 0.5 wt. % or even less than 0.3 wt. % have been reached. Before drying (after the crystallisation step), the humidity content is suitably in the range of 20 to 50 wt. %, such as 30 to 40 wt. %.

Preferably, the solid composition further comprises other reaction products resulting from depolymerisation of PET than BHET, including dimers, trimers, mono-(β-hydroxyethyl) terephthalate, bis-(β-hydroxyethoxy-ethyl)terephthalate. These reaction products will also be referred to as other terephthalate compounds. The total content of terephthalate compounds, also including BHET, is advantageously at least 98.0 wt. %, preferably at least 99.0 wt. %, more preferably at least 99.5 wt. % or even at least 99.7 wt. % in the final product. Other contaminations in the final dried product include water, ethylene glycol, as well as inorganic elements, such as sodium, iron, chloride and the like.

Typically, as based on HPLC tests, the solid composition comprises crystalline material and particularly merely one single crystalline form. While the process of granulating and drying is thus compatible with the maintenance of the crystalline form, it is not excluded that part of the BHET is converted into amorphous material. As such, the granulate can be considered to be polycrystalline in nature. The overall crystallinity of the solid composition is preferably at least 80 wt. %, more preferably at least 90 wt. % or even at least 95 wt. %, based on dry weight of the composition. An advantage of the crystalline form is its mechanical strength, as a result of which the risk of breakage and/or deformation during transport is reduced. A further advantage of the crystalline form is its reduced sensitivity, as compared to amorphous (i.e. powdery) material, for humidity. As a consequence, the risk for agglomeration during storage is lower than with amorphous material. The granules preferably have a size in the range of 1-10 mm. Granule size is characterized by sieving. Such a size has been found practical so as to arrive at an optimum with respect to drying time, dissolution time in ethylene glycol, melting time in molten BHET and transporting properties. The granulating step typically involves a size-reduction step starting from rather lumpy, agglomerated product. The granulating step could alternatively or additionally include an agglomeration step, in order to bind fines and individual crystallites. The granulating step is for instance achieved by means of extrusion, by pressing through a sieve, by pelletization and/or by means of a nibbler. The latter is deemed particularly useful when starting from a cake of crystalline material, such as a filter cake. A nibbler is a tool based on a rotor with strips screwed to it and a screening plate. In use, a filter cake is continuously fed to the nibbler. The infeed aperture of the nibbler is adjusted to match the size of filter cake. The nibbler rotor may rotate at a speed, for instance in the range of 50-100 rpm, for instance 80 rpm. The strips press the complete length of the filter cake against the screen. The shredded solids are collected in a tank or container. It is not excluded that another drying step, such as drying in an atmosphere in the range of 40-90° C. is performed as a pre-treatment prior to fluid bed drying.

Preferably, the dried granules have a pore volume of at least 0.30 cm$^3$/g, more preferably at least 0.40 cm$^3$/g or even at least 0.50 cm$^3$/g. it is deemed advantageous that the pore volume is smaller than 1.0 cm$^3$/g, preferably at most 0.80 cm$^3$/g, or even at most 0.70 cm$^3$/g. A relatively high pore volume is deemed advantageous so as to reduce the dissolution and melting time. A maximum in the pore volume is deemed advantageous so as to ensure sufficient stability of the granules and prevent disintegration into a powder that has less beneficial flow and transport properties. The pore volume is herein measured by means of mercury porosimetry, as known to the skilled person and standardized by ASTM D 4404-10. The pore volume may vary in dependence on the processing steps performed after crystallisation, the average particle size and furthermore the composition of the granulate. Initial experiments provided pore volumes in the range of 0.40-0.60 cm$^3$/g. The porosity (in %) is herein suitably at least 25%, more preferably at least 30%, or even at least 35%. Experimentally, porosities over 40%, such as between 40% and 50%, have been achieved. Additionally, it is deemed preferable that the granules have a bulk density in the range of 0.33-0.56 g/cm$^3$. The bulk density is defined as the density of the material including its pores, both inter-particle pores and intra-particle pores, as well as hollow spaces between individual granules. The bulk density is therefore a parameter representing bulk material as will be introduced into a mixing vessel prior to polymerisation or another reaction. The bulk density is more preferably in the range of 0.40-0.55 g/cm$^3$. The lower end of the range tends to depend largely on the presence of hollow spaces within the material. In one embodiment, with a fairly wide size distribution of the granules, the bulk density is at least 0.45 g/cm$^3$ or even at least 0.50 g/cm$^3$.

It has been found that the solid composition of the present invention has a dissolution time in heated ethylene glycol (particularly in a temperature range of 100-200° C., such as 120-195° C. or 130-190° C.) that is shorter than any other known or comparative solid composition of BHET. This is deemed highly beneficial on an industrial scale. Faster dissolution does not merely result in shorter production times, but the risk of keeping undissolved BHET material is significantly reduced. If some BHET material does not dissolve, it may end up as a contamination in the resulting polymer (such as PET). Any such contamination by solid particles will have a major impact on mechanical properties of the PET material, during and after processing thereof, such as blow moulding. Furthermore, any undissolved material may give rise to formation of agglomerates within a reactor system. Such agglomerates can reduce flow rates or even block flow, for instance in heat exchangers.

The solid composition of the present invention furthermore has a melting time in molten BHET that is shorter or the same than any other known or comparative solid composition of BHET. If the comparison is made with samples of equal size, the melting time in molten BHET is even significantly smaller than that of any other BHET composition. This again is highly beneficial on industrial scale, for the same reason as mentioned above. Moreover, the shortened melting or, where applicable dissolution time in BHET or, where applicable ethylene glycol has the benefit of providing the customer with a large process freedom.

Furthermore, the solid composition has in one embodiment thereof an angle of repose of less than 40 degrees, or even less than 38 degrees. The angle of repose is herein measured in accordance with the tilting method as specified hereinafter in more detail. The angle of repose is a parameter representing flowability of the material. Flowability is very important in industrial use.

The BHET of the present invention is preferably obtained from depolymerisation of a terephthalate polymer such as polyethylene terephthalate, polybutylene terephthalate, polypropylene terephthalate, polyethylene isoterephthalate, poly pentaerythrityl terephthalate as well as copolymers thereof such as a copolymer of polyethylene oxide and polybutylene terephthalate.

More preferably, it is obtained from depolymerisation of polyethylene terephthalate. Alternatively, the BHET may be obtained by means of a chemical reaction of a terephthalate source with a source of ethylene glycol. Known sources of terephthalate include dimethylterephthalate, terephthalic acid, terephthalonitrile as discussed in the background section. Known source of ethylene glycol include ethylene glycol and ethylene oxide.

When the BHET is obtained from depolymerisation, it is preferable that the BHET is crystallized only after crystallizing of dimer of BHET and its removal from the remaining mother liquid. This pre-treatment step has been found advantageous to prevent contamination of the crystalline BHET with ionic contaminants, such as ions of Na, K, Fe, Ca and the like. The removal of BHET dimer is moreover advantageous to ensure a sufficient purity of BHET without the need to use ethylene glycol in excess amounts during depolymerisation.

More preferably, dimer of BHET is present in the solid composition in an amount of at most 3.0 wt. %, and more preferably at most 2.5 wt. %, or even below 2.0 wt. %, such as 1.0-2.0 wt. %. It has been found that this level of impurity does not have any negative impact on the purity with regards to any cations that can be present in the mother liquid, such as iron ions.

In another aspect, the invention relates to a method of preparing a solid composition comprising at least 60.0 wt. % bis(2-hydroxyethyl) terephthalate (BHET) comprising the steps of: (1) providing crystalline material comprising at least 90.0 wt. % BHET, based on dry weight of the solid composition; (2) granulating the crystalline material and (3) fluid bed drying of the granulated crystalline material.

In a related aspect, the invention relates to a solid composition comprising at least 60.0 wt. % bis(2-hydroxyethyl) terephthalate (BHET), obtainable by granulating of crystalline BHET and subsequent fluid bed drying. The BHET content after drying is preferably at least 70.0 wt. %, more preferably at least 80 wt. % or even at least 90 wt. %. Other compounds in the composition include other terephthalate compounds. These are suitably present in an amount such that the solid composition in its entirety comprises at least 90 wt. % and more preferably at least 95 wt. % or even at least 98 wt. % of terephthalate compounds. After the fluid bed drying, the humidity content will generally be at most 5 wt. %, more preferably at most 2 wt. % or even at most 1 wt. %.

Such a solid composition preferably has the pore volume and/or density as specified hereinabove. However, it is not excluded that the method would be extended or varied so as to achieve a product still being advantageous but with a different porosity.

In one embodiment, such a solid composition is obtained by mixing crystalline BHET with crystalline dimer in a predefined ratio. The mixing is preferably carried out prior to granulating and fluid bed drying. Alternatively or additionally, terephthalic acid and/or a terephthalate salt could be mixed into the solid composition. The predefined ratio is more particularly defined in view of a subsequent polymerisation of PET, and would ensure fixation of a certain ratio, and would ensure adequate mixing of the different compounds in a melt or solution. Rather than mixing in compounds based only on terephthalic acid and hydroxyethyl-terephthalic acid (or those compounds in anion form), comonomers may be mixed into the solid composition, for instance based on hydroxy-butyl-terephthalic acid and the like.

In again a further aspect, the invention relates to a solid composition comprising at least 90.0 wt. %, bis(2-hydroxyethyl) terephthalate (BHET), as based on dry weight of the composition, and having a bulk density in the range of 0.33 to 0.56 g/cm$^3$, preferably 0.40 to 0.55 g/cm$^3$, or even 0.44-0.54 g/cm$^3$. The bulk density is herein determined as specified in more detail further down.

The invention further relates to the use of the solid composition of the invention in the polymerisation of BHET to polyethylene terephthalate (PET). It has been found that the BHET in the solid composition has the required purity for polymerisation and has appropriate flowability.

Preferably, said use comprises the step of dissolving said solid composition in ethylene glycol or melting said composition when submerged in a melt of BHET. These two options are common ways of creating an initial mixture of reagents. One advantage of the use of the present solid composition is that it will not sink into the ethylene glycol or BHET, but remain on the surface. This is believed to contribute to a higher rate of dissolution and further may reduce a risk that part of the BHET remains undissolved. More preferably, said solid composition has a melting time at 140° C., when submerged in molten BHET, of less than 30 seconds, wherein said solid composition is present as granules with a size limit of 5 mm as measured by sieving, and in an amount of 5 wt. % of the molten BHET. It is observed for sake of clarity that it is not excluded that any further compound (such as a solvent, reagent or additive) may be present in the solvent (ethylene glycol) or the molten BHET in which the solid composition gets dissolved or molten. One typical additive is for instance water which may act as a catalyst in the polymerisation, or can act as a solvent for a catalyst. It is furthermore not excluded that the solid composition of the present invention is used for the preparation of a copolymer or another polymer than PET.

These and other aspects of the invention will be further elucidated with reference to the examples and figures. It is observed for clarity that any preferred embodiment as discussed above applies to any and all of the claim categories and aspects, including the solid composition, the preparation method thereof, and its use, even when not discussed explicitly for sake of avoiding repetition.

MEASUREMENT METHODS

Figure 1:
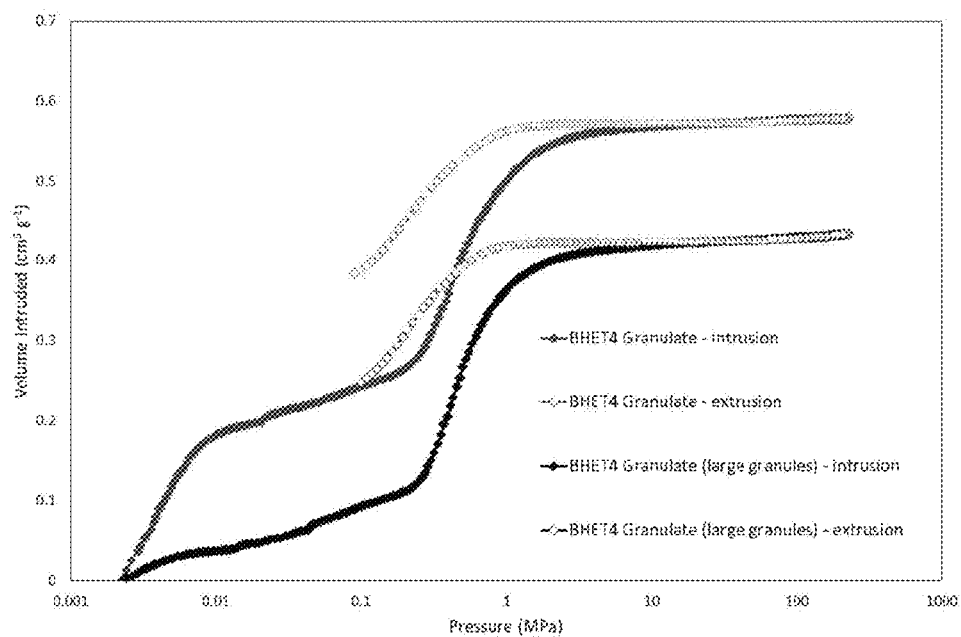
FIG. 1 is a graph of the intrusion and extrusion volumes of the solid composition of the invention, and a larger granule fraction thereof in function of the applied pressure in the course of mercury intrusion porosimetry.

In the following, reference is made to BHET for several solid compositions comprising at least 90 wt. % BHET (and hereinafter also referred to as BHET).

Purity 25 mg BHET is dissolved in 50 ml 100% acetonitrile, and measured with the HPLC "Agilent Technologies 1100 Series" with a "XBridge C8 3.5 µm, 4.6×150 mm" column. The detector is a DAD 242 nm.

The reported results (in table 1) are averages of Duplo measurements.

Bulk Density

The bulk density (below also referred to with p) is the weight of the material in a container of a certain volume. The value in the table is an average of a Duplo measurement. The protocol comprises:
1. Tare a weighing scale with a 1000 ml measurement cylinder.
2. Fill the cylinder with solid BHET and note the weight of the BHET.
3. Determine the added volume of the BHET, by reading it from the measuring cylinder.

4. $$\rho \left[ \frac{g}{cm^3} \right] = \frac{BHET[g]}{\text{Filled volume } [cm^3]}$$

A 1000 ml measurement cylinder is used, so as to avoid wall-effects of the cylinder that would render the method less accurate. However, the determination of added volume sets a limit to the precision.

Skeletal Density

Skeletal density is determined with gas-pycnometry. The skeletal density takes into account that the density of the particles is reduced by the encapsulation of air bubbles. The protocol is:

The samples are degassed in vacuum at 25° C. for 16 h prior to measurement. The measurement was performed in accordance with ISO 12154: 2014 with the Quantachrome Ultrapycnometer 1000 at 25° C. A sample size of 150 cm³ was used due to the large particle size distribution.

The reported values are averages of ten successive dependent measurements over a single representative sample with a maximum variation over these ten successive measurements of less than 0.08%. The estimated inaccuracy is determined using a standard deviation over a quality control material.

Porosity

The pore volume is determined with Hg-porosimeter. Prior to the mercury intrusion measurements, the samples were degassed in vacuum at 25° C. for 16 h. Subsequently, the intrusion and extrusion curves were recorded on a Micromeritics Autopore 9505 analyzer, applying pressures from 0.002 MPa up to 220 MPa. This pressure is converted to the pore diameter using the Washburn equation, wherein a value of 140° is used for the contact angle. The measurement was performed as in accordance with ASTM D 4404-10. Due to the limited size of the cell used in the mercury intrusion porosimetry and in order to have a fair comparison among the samples, only particles with a size smaller dan 0.6 mm were used for the test.

The porosity (%) is calculated on the basis of these measurements.

Apparent Density

The apparent density is the density calculated on the basis of the mercury intrusion porosimetry.

Angle of Repose

The angle of repose is defined as the angle from a horizontal plate to the free surface of a powder under gravitational force. The so-called tilting method is used for the measurements. It is known that this tilting method generally results in higher values than other methods such as the injection method. Use was made of a drum with a diameter of 153 mm and a height of 45 mm. Approximately 200 ml of sample was placed inside the drum. The rotation speed of the drum was set to 6.4 rpm. Three photographs are made during rotation of the drum and the angle of repose is determined optically from each of the photographs. The provided value is the average.

Rate of Dissolution in Ethylene Glycol

The dissolution of BHET is measured at two temperatures: $T_1=140°$ C. and $T_2=180°$ C. The measurement method protocol is:

First, heat 95 g of ethylene glycol (EG) to $T_1$ or $T_2$ in a 250 ml beaker glass closed off with a watch glass or aluminium foil. A heating plate of the type IKA C-MAG HS7 was used with the stirrer speed set at 1.5, on a scale up to 6. With a thermocouple, it was ensured that the solution did not overheat. When the EG has reached the specified temperature (T1 or T2), remove the watch glass or the aluminium foil and add 5 g solid BHET in one uninterrupted movement. The settings for temperature and stirring speed remain unchanged. The temperature drops due to the implementation of BHET at room temperature, which the thermocouple will respond to.

Then, the dissolution time is registered: With a video camera, the introduction of BHET and its dissolving in EG is recorded. These recordings are studied in slow motion to visually determine when all solids are dissolved.

The value in the table is an average of a Duplo measurement.

For the BHET in accordance with the invention, the measurement has been carried out on the basis of BHET as obtained after fluid bed drying and on the basis of samples on which a size reduction treatment was carried out to arrive at a size of 5 mm as defined by sieving.

Rate of Melting in Molten BHET

The melting of BHET is measured at two temperatures: $T_1=140°$ C. and $T_2=180°$ C. The measurement method comprises the steps of:

First, the BHET melt is prepared. Thereto 47.5 g of BHET is heated to $T_1$ or $T_2$ in a 250 ml Erlenmeyer which is submerged in a paraffin oil bath. This results in formation of the melt. The Erlenmeyer with BHET is kept at least 15 min. in the oil bath to ensure a homogenous temperature of the melt. Both the melt and the oil are stirred with a stirring speed of 1.5 (on a scale up to 6) on a heating plate of the type IKA C-MAG HS7. A thermocouple is used to keep the oil bath at constant temperature.

As a second step, solid BHET is added to the BHET melt. 2.5 g solid BHET is added in one uninterrupted movement. The settings for temperature and stirring speed remain unchanged. Then, the melting time is measured, using a video camera: The introduction of BHET and its melting is recorded. These recordings are studied in slow motion to visually determine when all solids are dissolved.

For the BHET in accordance with the invention, the measurement has been carried out on the basis of BHET as obtained after fluid bed drying and on the basis of samples on which a size reduction treatment was carried out to arrive at a size of 5 mm as defined by sieving.

The value in the table is an average of a Duplo measurement.

EXAMPLES

Example 1: Preparation of the BHET According to the Invention

A mixture of flakes of polyethylene terephthalate (PET), ethylene glycol (EG) and a catalyst was used in a mutual ratio in the range. In an example on laboratory scale in a 100 mL flask, 1 g of dry catalyst complex was used in combination with 5 g of PET and 50 g of EG. The catalyst complex was prepared by starting from magnetite nanoparticles (size 5 nm), trisilanolpropyl ($C_3H_7Si(OR)_3$, wherein R (ethyl) and (bim)$FeCl_4$ or (bim)Cl. Herein bim refers to butylimidazolium. The catalyst complex was prepared by a reaction of the (bim) $FeCl_4$ or (bim) Cl with the trisilanolpropyl. The resulting functionalized propyltrisilanol was brought into contact with the nanoparticles so as to form an aggregate in the manner specified in WO2017111602, which is included herein by reference. However, the use of alternative catalysts is not excluded. The catalyst complex dispersion was homogenised by shaking for 5 minutes by hand. To 10 g of catalyst complex dispersion 41 g of EG was added and the liquids were shortly mixed by hand to homogenise the dispersion. Then, 5 g of PET flakes were added and the round bottom flask was placed in the heating set up. The PET flakes were prepared from coloured PET bottles such as commercially available blue coloured bottles and red coloured bottles. The heating was started and within 20 minutes, the reaction mixture had reached the reaction temperature of 170-200° C.

The depolymerisation was repeated in a 1000 liter vessel. The degradation reaction was carried out at a temperature in the range of 180-210° C. The concentration of the catalyst complex was about 0.5 wt. %, which was not very critical. After a predefined duration of the reaction, for instance 60-180 minutes, the reaction mixture was cooled down. Water was added and the mixture was led to a centrifuge for separation. This treatment resulted in a first hydrophilic solution and a second phase. The hydrophilic solution contained a mixture of water and the solvent, ethylene glycol. The second phase was in the form of a slurry, which contained a significant portion of solid material. At least 95% of the flow entering the centrifuge became hydrophilic solution. Typically, this was over 98%, or even over 99%. The hydrophilic solution was led via a membrane filter to remove solid material to an adsorbant, i.e. active coal.

The hydrophilic solution was transferred to a dimer crystallisation stage, which was in the example a mixing vessel that is provided with temperature regulation means for bringing and keeping the crystallizing solution at a predefined temperature, for instance in the range of 50-70° C., such as 57-64° C., for instance 60° C. The exact temperature will depend on the concentration of the dimer, the ratio between water and ethylene glycol and the desired residence time. After a sufficient degree of crystallisation, the resulting combination of first mother liquid and dimer crystals was transferred to a separator, for instance a filtration unit.

Downstream thereof, the BHET is crystallized and recovered in a further separator. Crystals were obtained in a purity of more than 90 wt. %, based on dry weight. In the example used, the crystallisation of BHET occurred at a lower temperature relative to the dimer crystallisation. The BHET crystals were thereafter washed with water, so as to remove any adsorbed mother liquid. The material has a humidity content of 28-40 wt. % and is in the form of a cake.

A test was carried out on labscale to identify purity. BHET crystalline material was obtained starting from a hydrophilic solution of 520 gram containing 35.4 gram BHET (6.8 wt. %), 3.6 gram dimer (10.8 wt. % relative to BHET) and 50 ppm Fe. The wet BHET was washed and thereafter dried in a laboratory scale drying equipment. The overall dimer content in the dried BHET was 1.5 wt. %, and the Fe content 20 ppm.

Example 2

500 gram of said crystallized and washed material was thereafter subjected to size reduction and drying. Size reduction occurred by means of pressing through a sieve with a sieve of 5 mm (opening). The resulting material—granules—was thereafter dried in a fluid bed dryer, with air as the carrier gas. The temperature of the carrier gas was 90° C. The flow rate was initially in the range of 0.9-1.2 kg/(m²·s) and typically reduced to 0.8 kg/(m²·s) after 10 minutes. Use was made of a batch type of a so-called shaking fluid bed dryer suitable for 1 liter of product per batch. The drying time was between 14 and 20 minutes. The resulting humidity content reduced from 1.5 wt. % to 0.1 wt. % as a function of the drying time. The material was white. No contamination was visible.

Example 3

Crystalline BHET material as obtained in Example 1 with a humidity content of 36 wt. % and in the form of a cake was processed by means of a nibbler for size reduction to obtain granules. Thereafter, the resulting, granulated material was subjected to fluid bed drying. A white material was obtained without any visible contamination. This material was further evaluated.

Comparative Example 1

The crystallized BHET obtained in example 1 after the washing step was dried by means of vacuum drying.

Comparative Example 2

BHET was obtained from Sigma-Aldrich (product number 465151) and was delivered in a poly bottle. The purity was at least 94.5 wt. %. (GC) according to specifications of the supplier.

Evaluation of Shape and Purity

An evaluation was made of the shape, particle size distribution and the purity of the material. The results are shown in Table 1. The material of the invention was a granulate, wherein individual particles had varying size and were characterized by irregular shapes and a non-smooth surface. In one test, a small size distribution was chosen from the material. It was found that the purity of this size fraction did not deviate from the overall purity. The purity is herein measured on the basis of HPLC. The material of comparative example 1 was stone-like, with rather smooth surfaces. Purity measurements demonstrated a larger variation. The material of comparative example 2 was in the form of flakes. The purity turned out higher than the minimum purity indicated by the supplier.

TABLE 1 measured parameters

| Example | Shape | Shape characterisation | Particle dimensions and size distribution | Purity (wt. %), HPLC |
|---|---|---|---|---|
| 3-1 | Granulate | Non-smooth surface, irregular shapes (spheres, elongated spheres) | Wide size distribution | 97.6 |
| 3-2 | Granulate | | | 95.5 |
| 3-3 | Granulate | Non-smooth surface, irregular shapes (spheres, elongated spheres) | Small size distribution: 4-6 mm diameter | 96.6 |
| Comp 1-1 | Stone-like | Smooth surface, spheres | Wide size distribution: Fines - cm scale | 93.3 |
| Comp 1-2 | Stone-like | | | 98.9 |
| Comp 2-1 | Flakes | Smooth surface, flat flakes | Wide size distribution: cm scale | 98.7 |
| Comp 2-2 | Flakes | | | 98.7 |

The wide size distribution of the examples according to the invention were further specified as that 99% was smaller than 6.3 mm and 70% was smaller than 2.4 mm, as based on particle sieving. In further experiments using laser diffraction, using 0 bar venturi pressure, the volume particle size distribution as specified in Table 2 was measured. The data are herein averages of two separate measurements:

TABLE 2

| | meaning | Value |
|---|---|---|
| $D_o$ | Minimum particle size | 0.14 mm |
| $D_{10}$ | 10% of particle volume smaller than the tabled value | 0.65 mm |
| $D_{50}$ | Median particle size | 1.30 mm |
| $D_{90}$ | 90% of particle volume smaller than the tabled value | 2.40 mm |
| $D_{100}$ | 100% of particle volume is smaller than the tabled value | 3.50 mm |
| D [4, 3] | Volume weighted mean diameter | 1.42 mm |
| Span | Distributed width, calculated as $(D_{90} - D_{10})/D_{50}$ | 1.4 (—) |
| Mode 1 | Modal size, particle diameter present with highest frequency | 1.4 mm |

It is observed that the values obtained with the laser diffraction measurements do not include particles with a size beyond 3.5 mm, which are present. It is estimated that the results are applicable for the 70% that was sieved through the 2.36 mm sieve. Hence, it can be concluded that the granulate in accordance with the invention, at least in one preferred embodiment, has a mean diameter, as measured by laser diffraction (excluding particles beyond 3.5 mm), in the range of 1.2-1.6 mm, said mean diameter being defined as the volume weighted mean diameter $((\Sigma n_i D_i^4)/(\Sigma n_i D_i^3))$. Preferably, said mean diameter is in the range of 1.3-1.5 mm. The mean diameter is in the range of 1.1-1.5 mm, preferably 1.2-1.4 mm. The distribution width is in the range of 1.3-1.5.

Test of Densities and Porosity

Measurements of density and porosity were hereinafter carried out as described above. Results are shown in Table 3. For the material of the invention, a separate test was carried out with relatively large granules. The larger granules fraction corresponds to the fraction 1-3 indicated in Table 1. The general fraction additionally includes smaller granules. In other words, the larger granules fraction is a portion of the general fraction. The sample including larger granules corresponds better to the particle size present for the comparative samples.

TABLE 3 densities (values are averaged), pore volume and porosity. Sample 1A indicates a fraction of sample 1 based on large granules.

| Example | Bulk Density (g/cm$^3$) | Skeletal density (g/cm$^3$) | Apparent density (g/cm$^3$) | Pore volume (cm$^3$/g) | Porosity (%) |
|---|---|---|---|---|---|
| 3 | 0.53 | 1.337 | 1.34 | 0.58 | 44% |
| 3A | — | — | 1.35 | 0.43 | 37% |
| Comp 1 | 0.64 | 1.301 | 1.33 | 0.04 | 5% |
| Comp 2 | 0.59 | 1.371 | 1.40 | 0.04 | 5% |

The skeletal densities are in the range of 1.301-1.371 g/cm$^3$. The maximum absolute error for the measurement is approximately 0.005 g/cm$^3$. Therefore, although the differences are small, the skeletal densities of all samples are significantly different. These differences in density can be caused by impurities and/or by inaccessible voids in the materials.

The bulk densities are significantly lower than the skeletal densities. This is the result of the presence of pores, both intra-particle pores and inter-particle pores. A further contribution to the bulk density is obtained from hollow spaces between the samples when filling the beaker. Given that the particles of the comparative examples are larger, the contribution of the hollow spaces is more significant for the comparative examples. Still, it is apparent from Table 1 that the bulk density for the sample of the invention is lower than that of the comparative examples. This is due to the increased porosity.

It is immediately visible that the pore volume of the sample of the invention is significantly larger than that of the comparative samples. The pore volume of the larger granules fraction is lower. It is understood by the inventors that selective variation of the pore volume can be obtained by means of the settings of the processing steps after crystallisation (size reduction and fluid bed drying). Mercury intrusion and extrusion curves for the sample of the invention are shown in FIG. 1 Herein, the intruded volume (cm$^3$/g) is shown as a function of the applied pressure (MPa). The extrusion curves are shown with open dots (starting at 0.1 MPa), the intrusion curves with massive dots. The upper curves relate to the normal samples, the lower curves relate to the samples obtained from larger granules. The curves show initial intrusion from a low pressure of approximately 0.002 MPa up to approximately 0.05 MPa. This initial intrusion should be attributed to the rearrangement of particles and the filling of inter-particle voids. It can be easily seen that this step is much lower for the larger granules fraction. The intrusion curves show a very similar second intrusion step ranging from approximately 0.1-10 MPa. Such contribution presumably is to be attributed to intra-particle void contribution. From a pressure of 10 MPa upwards a nice plateau is reached. This observation is an indication that all porosity of pores of at least 6 nm is adequately assessed. The pore size of 6 nm is the lower limit of the mercury intrusion porosimetry technique.

Quantitative information on the total pore volume and the porosity derived thereof is summarized in Table 3. Since compression occurs, use is made of results at different pressures so as to exclude the compression in the calculations.

The obtained apparent densities can be correlated to the skeletal densities. Only very minor differences are obtained, with a maximum relative deviation of 5%.

Figure 2:
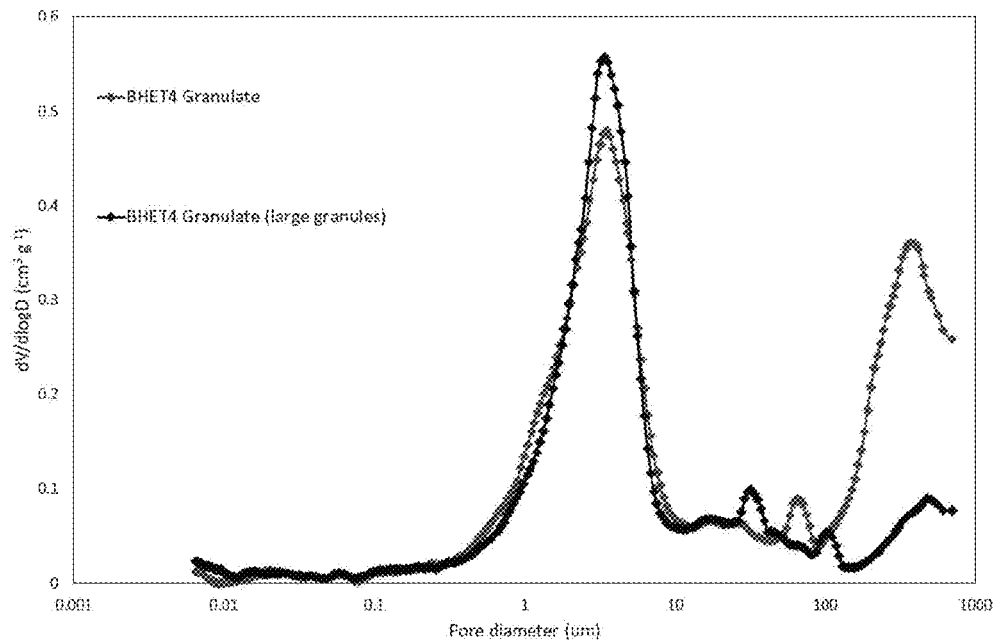
FIG. 2 is a graph of the pore size distribution that is derived from the intrusion curve as shown in FIG. 1.

Pore size distributions have been derived from the intrusion curves. The result is shown in FIG. 2. Two major contributions are therein visible. First of all, there is an inter-particle contribution from 50-700 μm, with a mode around 415 μm. This can be attributed to the filling of inter-particle pores. A second contribution ranges from approximately 0.3-10 μm with a mode at 4 μm. This contribution should be attributed to the filling of intra-particle pores.

Intrusion curves for the comparative examples are at significantly lower levels reaching up to a maximum of approximately 0.04 cm$^3$/g, rather than 0.4 cm$^3$/g for the larger granule fraction. In the derived pore size distributions, the intra-particle contribution in the range of 0.03-10 μm is almost entirely absent.

Evaluation of Flow, Melting and Dissolution Behaviour

The behaviour of the material upon melting in molten BHET and dissolution in ethylene glycol was tested. This behaviour is important for the intended re-polymerisation of the material. Results are shown in Table 4. Furthermore, the angle of repose is indicated. This parameter is indicative of the flow behaviour. Results are shown in Table 4. The test was carried out in duplo. The sample of the invention was furthermore measured twice: for the second experiment a size reduction was carried out. Moreover, the test is carried out at two different temperatures.

TABLE 4 dissolution and melting times

Dissolution times/melting times in seconds in

| Example | ethylene glycol at 140° C. | ethylene glycol at 180° C. | molten BHET at 140° C. | molten BHET at 180° C. | Remarks |
| --- | --- | --- | --- | --- | --- |
| 3-1 | 16 | 4 | 57 | 25 | Without size reduction |
| 3-2 | 8 | 7 | 54 | 19 | Without size reduction |
| 3-3 | 7 | 4 | 23 | 7 | After size reduction to 5 mm |
| 3-4 | 6 | 3 | 19 | 8 | After size reduction to 5 mm |
| Comp 1-1 | 57 | 23 | 93 | 35 | |
| Comp 1-2 | 46 | 29 | 89 | 41 | |
| Comp 2-1 | 16 | 12 | 38 | 15 | |
| Comp 2-2 | 20 | 9 | 47 | 16 | |

The results in Table 4 indicate that melting and dissolution is worst for comparative example 1. This material includes the same crystallized BHET as that of the invention, but is thereafter processed in a different manner arriving at low porosity rather than high porosity. The melting and dissolution times for the material of the invention without size reduction and that of comparative example 2 are comparable. However, it should be understood that this is not deemed an appropriate comparison, as the volume per particle of the samples 3-1 and 3-2 of the invention is larger than that of the comparative examples. When performing a further size reduction to arrive at comparable volumes, the dissolution and melting times of the material of the invention are clearly shorter.

TABLE 5 angle of repose. All values in degrees. The standard deviation indicates the 95% confidence interval.

| | Measurement | | | | Standard |
| Example | 1 | 2 | 3 | Average | deviation |
| --- | --- | --- | --- | --- | --- |
| 3 | 35.4 | 36.9 | 37.3 | 36.5 | 2.5 |
| Comp 1 | 45.0 | 48.0 | 42.2 | 45.1 | 7.2 |
| Comp 2 | 48.3 | 50.6 | 48.6 | 49.2 | 3.1 |

Table 5 indicates the angles of repose. Therein, the 95% confidence interval is calculated according to the students-t-method with 3 observations. Based on the confidence interval, the Comparative Example 2 is significantly different from that of the invention. The Comparative Example 1 is quite different. However, due to the higher standard deviation, no statement can be made as to the statistically significant difference. The material of the invention has the lowest angle and is thus best flowable.

These results correspond with the observations as to shape. The material of comparative example 2 is in the form of flakes. This shape can be expected to have worst flowability. Another important factor is the particle size distribution. A narrow particle size distribution will promote a better flowability. The material of Comparative example 1 has the broadest particle sized distribution of all samples. Hence, it is not surprising that its flow behaviour is not good.

This application is based on Netherland Patent Application Serial No. 2023686 filed with Netherland Patent Office on Aug. 22, 2019, the entire contents of which are hereby incorporated herein by reference.

The invention claimed is:

1. A solid composition comprising at least 90.0 wt. % bis (2-hydroxyethyl) terephthalate (BHET), as based on dry weight and having a pore volume in the range of 0.20 to 1.0 cm$^3$/g.

2. The solid composition according to claim 1, wherein at least 80 wt. % of the BHET is present in crystalline form.

3. The solid composition according to claim 1, having a bulk density in the range of 0.33-0.56 g/cm$^3$.

4. The solid composition according to claim 1, wherein the solid composition has a humidity content of at most 5.0 wt. %, more preferably at most 2.0 wt. %, more preferably at most 1.0 wt. %.

5. The solid composition according to claim 1, wherein the composition comprises at least 95.0 wt. % BHET, more preferably 96.0 wt. % BHET and by further preference at least 97.0 wt. % BHET, as based on dry weight.

6. The solid composition according to claim 1, wherein the composition further comprises dimer of bis (2-hydroxyethyl) terephthalate.

7. The solid composition according to claim 1, wherein the BHET is in the form of granules.

8. The solid composition as claimed in claim 1, wherein the composition is obtainable by granulating of crystalline BHET and subsequent fluid bed drying.

9. The solid composition as claimed in claim 7, wherein the granulate has a size in the range of 0.1 to 10 mm, preferably 0.5 to 8 mm as defined by sieving.

10. The composition as claimed in claim 1, wherein said solid composition has a melting time at 140° C., when submerged in molten BHET, of less than 30 seconds, wherein said solid composition is present as granules with a size limit of 5 mm as defined by sieving, and in an amount of 5 wt. % of the molten BHET.

11. The composition as claimed in claim 1, wherein the BHET is obtained from depolymerization of polyethylene terephthalate.

12. A method of preparing a composition comprising at least 90.0 wt. % bis (2-hydroxyethyl) terephthalate (BHET) and having a pore volume in the range of 0.20 to 1.0 cm$^3$/g, comprising the steps of:
Providing crystalline material comprising at least 90.0 wt. % BHET, based on dry weight;
Granulating the crystalline material;
Fluid bed drying of the granulated crystalline material.

13. The method as claimed in claim 12, wherein the provision of the crystalline material comprises crystallizing said BHET and washing the crystallized BHET with a volatile medium, such as water.

14. The method as claimed in claim 12, wherein the step of providing the crystalline material comprising at least 90.0 wt. % BHET comprises the steps of:
Providing a solution of at least BHET and a dimer of BHET in a mixture of water and ethylene glycol;
Selectively crystallizing the dimer of BHET and separating said dimer of BHET from a remaining mother liquid, and thereafter;
Crystallizing the BHET from said mother liquid.

15. The method as claimed in claim 14, wherein the selective crystallization of dimer of BHET reduces a concentration of dimer of BHET in the mother liquid to at most 3.0 wt. %, preferably at most 2.5 wt. % relative to the BHET in the mother liquid.

16. The method as claimed in claim 12, wherein the granulating comprises breaking up of a cake of the crystalline material, for instance by means of a nibbler.

17. The method as claimed in claim 12 further comprising polymerisation of the composition of claim 12 to polyethylene terephthalate.

18. The method as claimed in claim 17, comprising the step of dissolving said composition in ethylene glycol or melting said composition when submerged in a melt of BHET.

19. The method as claimed in claim 18, wherein said composition has a melting time at 140° C., when submerged in molten BHET, of less than 30 seconds, wherein said composition is present as granules with a size limit of 5 mm as defined by sieving, and in an amount of 5 wt. % of the molten BHET.

* * * * *